(12) United States Patent
Kim

(10) Patent No.: US 12,004,921 B2
(45) Date of Patent: Jun. 11, 2024

(54) SCAN GUIDE PROVIDING METHOD AND IMAGE PROCESSING DEVICE THEREFOR

(71) Applicant: OSSTEMIMPLANT CO., LTD., Seoul (KR)

(72) Inventor: Sulho Kim, Seoul (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 358 days.

(21) Appl. No.: 17/436,889

(22) PCT Filed: Mar. 3, 2020

(86) PCT No.: PCT/KR2020/003024
§ 371 (c)(1),
(2) Date: Sep. 7, 2021

(87) PCT Pub. No.: WO2020/204366
PCT Pub. Date: Oct. 8, 2020

(65) Prior Publication Data
US 2022/0160476 A1    May 26, 2022

(30) Foreign Application Priority Data
Mar. 29, 2019  (KR) .................... 10-2019-0036899

(51) Int. Cl.
| | |
|---|---|
| *A61C 9/00* | (2006.01) |
| *G06T 1/00* | (2006.01) |
| *G06T 7/00* | (2017.01) |
| *G06T 7/50* | (2017.01) |

(52) U.S. Cl.
CPC .......... *A61C 9/0053* (2013.01); *G06T 1/0007* (2013.01); *G06T 7/0012* (2013.01); *G06T 7/50* (2017.01); *G06T 2207/10028* (2013.01); *G06T 2207/30036* (2013.01)

(58) Field of Classification Search
CPC .................... A61C 9/0053; A61C 9/00; G06T 2207/30036; G06T 7/0012; G06T 1/0007; G06T 7/00; G06T 7/50; G06T 2207/10028; G06T 1/00
See application file for complete search history.

(56) References Cited

U.S. PATENT DOCUMENTS

| | | | | |
|---|---|---|---|---|
| 9,683,835 | B2 * | 6/2017 | Kopelman | ............... A61C 5/77 |
| 9,830,688 | B2 * | 11/2017 | Levin | ..................... A61B 6/145 |
| 2013/0329020 | A1 | 12/2013 | Kriveshko et al. | |

(Continued)

FOREIGN PATENT DOCUMENTS

| | | |
|---|---|---|
| CN | 102429740 A | 5/2012 |
| CN | 106061357 A | 10/2016 |
| CN | 108309493 A | 7/2018 |

(Continued)

*Primary Examiner* — Tuan H Nguyen
(74) *Attorney, Agent, or Firm* — NKL Law; Jae Youn Kim

(57) ABSTRACT

Disclosed are a scan guide providing method and an image processing device therefor. A scan guide providing method according to an embodiment comprises the steps of: displaying, on a scan screen, a guide scan path for providing a scanning strategy of an intraoral scanner; tracking a user scan path actually scanned, along the guide scan path, by the intraoral scanner; and displaying the tracked user scan path together with the guide scan path.

19 Claims, 13 Drawing Sheets

(56) References Cited

U.S. PATENT DOCUMENTS

2017/0056136 A1   3/2017   Adamson et al.

FOREIGN PATENT DOCUMENTS

| | | |
|---|---|---|
| CN | 108333746 A | 7/2018 |
| EP | 3689218 A1 | 8/2020 |
| JP | 10-005248 A | 1/1998 |
| JP | 2008-537494 A | 9/2008 |
| JP | 2017-513597 A | 6/2017 |
| KR | 10-2010-0066538 A | 6/2010 |
| KR | 10-2015-0082428 A | 7/2015 |

* cited by examiner

SCAN GUIDE PROVIDING METHOD AND IMAGE PROCESSING DEVICE THEREFOR

TECHNICAL FIELD

The present disclosure relates to an intraoral scanner and an image processing technique for scanning.

BACKGROUND ART

A scan guide may be provided to accurately photograph teeth through an intraoral scanner. However, such a scan guide is provided in a separate document or on a web page. Therefore, when a user does not read product guides, the user may not be aware of the presence of the scan guide. Even if the user is aware of the presence of the scan guide, there is no way to check whether photographing is appropriately performed according to the scan guide.

DISCLOSURE

Technical Problem

An embodiment provides a scan guide providing method of providing a scan guide through a scan screen so that a user may check whether photographing is performed according to the scan guide, and an image processing device therefor.

Technical Solution

According to an embodiment, a scan guide providing method includes displaying, on a scan screen, a guide scan path providing a scanning strategy of an intraoral scanner, tracking a user scan path actually scanned through the intraoral scanner along the guide scan path, and displaying the tracked user scan path together with the guide scan path.

The displaying of the guide scan path on the scan screen may include displaying, on a screen, guide scan paths set in advance for respective manufacturers of intraoral scanners.

The displaying of the guide scan path on the scan screen may include rotating the guide scan path according to a user's manipulation or moving the guide scan path to the same viewpoint as a position actually photographed through the intraoral scanner and displaying the guide scan path on a screen.

The displaying of the guide scan path on the scan screen may include rotating the guide scan path in real time and displaying the guide scan path on a screen in synchronization with a position actually photographed by the intraoral scanner.

The tracking of the user scan path may include creating a depth image by reconstructing a two-dimensional (2D) image acquired through scanning by the intraoral scanner; connecting central points or main points of objects constituting the depth image; and generating the user scan path by detecting intersection points from the central points or main points on the objects to a position on a surface of a three-dimensional (3D) object and connecting the detected intersection points. In this case, the tracking of the user scan path may further include correcting the user scan path by connecting points spaced a predetermined distance from the detected intersection points.

The tracking of the user scan path may include generating the user scan path by connecting central points on objects constituting a three-dimensional (3D) image acquired through scanning by the intraoral scanner.

The displaying of the tracked user scan path together with the guide scan path may include equalizing a scale of the tracked user scan path with a scale of the guide scan path and displaying the user scan path to match the guide scan path.

The scan guide providing method may further include displaying the user scan path on image data acquired through scanning by the intraoral scanner.

The scan guide providing method may further include providing a user interface through which whether to display a scan guide or not is set by a user, and providing a user interface through which a transparency of the scan guide is set by the user.

The scan guide providing method may further include comparing and analyzing the user scan path and the guide scan path to each other and providing at least one of a comparison and analysis result and a warning signal generated as the result.

According to another embodiment, an image processing device includes a data acquisition unit configured to acquire, from the intraoral scanner, image data acquired by scanning the inside of a user's mouth or an intraoral model, an output unit configured to display the image data acquired from the intraoral scanner and a guide scan path providing a scanning strategy of the intraoral scanner, and a control unit configured to receive and image-process the image data acquired by the data acquisition unit and providing the guide scan path to the output unit.

The output unit may rotate the guide scan path according to a user's manipulation or move the guide scan path to the same viewpoint as a position actually photographed through the intraoral scanner and display the guide scan path on a screen.

The output unit may rotate the guide scan path in real time and display the guide scan path on the screen in synchronization with a position actually photographed by the intraoral scanner.

The output unit may display, on the screen, a user interface through which whether to display a scan guide or not is set by a user and a user interface through which a transparency of the scan guide is set by the user.

The control unit may configure a screen by tracking a user scan path actually scanned through the intraoral scanner along the guide scan path and matching the tracked user scan path to the guide scan path, and the output unit may display the user scan path on the screen together with the guide scan path.

The control unit may create a depth image by reconstructing a two-dimensional (2D) image acquired through scanning by the intraoral scanner, connect central points or main points on objects constituting the depth image, and generate the user scan path by detecting intersection points from the central points or main points on the objects to a position on a surface of a three-dimensional (3D) object and connecting the detected intersection points. In this case, the control unit may correct the user scan path by connecting points spaced a predetermined distance from the detected intersection points.

The control unit may generate the user scan path by connecting central points on objects constituting a three-dimensional (3D) image acquired through scanning by the intraoral scanner. The control unit may equalize a scale of the tracked user scan path with a scale of the guide scan path and match the user scan path to the guide scan path.

The output unit may display the user scan path on image data acquired through scanning by the intraoral scanner. The control unit may compare and analyze the user scan path and the guide scan path to each other and provide at least one of a comparison and analysis result and a warning signal generated as the result.

Advantageous Effects

According to a scan guide providing method and an image processing device therefor, a scan guide providing scan strategies using an intraoral scanner may be provided through a scan screen of a scan program, thereby enabling a user to check a guide scan path through the scan program.

In addition, a user scan path for tracking a scan direction in real time may be displayed in a guide scan path together with acquired image data so that a user may check whether photographing is appropriately performed according to the guide scan path. Accordingly, more accurate scan image data may be acquired. Furthermore, scanning may be trained through the intraoral scanner.

MODES OF THE INVENTION

Figure 1:
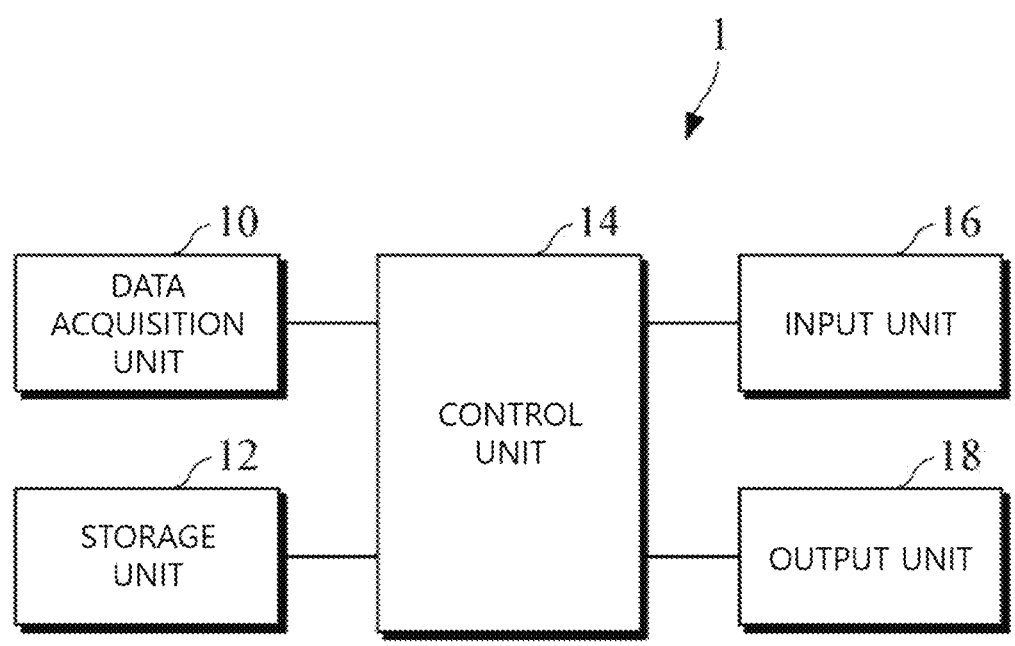
FIG. 1 is a diagram illustrating a configuration of an image processing device according to an embodiment of the present disclosure.

Advantages and features of the present disclosure and methods of achieving them will be apparent from embodiments described below in detail in conjunction with the accompanying drawings.

However, the present disclosure is not limited to these embodiments and may be embodied in many different forms. Rather, these embodiments are provided so that this disclosure will be thorough and complete and will fully convey the concept of the present disclosure to those of ordinary skill in the art. The present disclosure should be defined by the scope of the claims. The same reference numerals refer to the same components throughout the specification.

When embodiments of the present disclosure are described, well-known functions or constructions are not described in detail if it is determined that they would obscure the present disclosure due to unnecessary detail. Terms to be described below are defined in consideration of functions of embodiments of the present disclosure but may be differently defined according to users' or operators' intentions, precedents, or the like. Therefore, these terms should be defined based on the whole context of the present specification.

Combinations of blocks of a block diagram and operations of a flowchart attached herein may be performed by computer program instructions (an execution engine), and because these computer program instructions may be included in a universal computer, a special computer, or a processor of another programmable data processing device, the instructions performed through a computer or the processor of the other programmable data processing device will generate a means for performing the functions described in each block of the block diagram or each operation of the flowchart.

The computer program instructions may be stored in a computer usable or readable memory oriented to a computer or other programmable data processing devices to implement functions in a particular way. Thus, an article of manufacture, including an instruction means for performing the function of each block of the block diagram or each operation in the flowchart, may be produced by the instructions stored in the computer usable or readable memory.

Because the computer program instructions may be stored in a computer or other programmable data processing devices, the functions of the blocks of the block diagram and the operations of the flowchart may be provided by these instructions performing a series of operations in the computer or the other programmable data processing devices to produce a process executable by the computer to generate computer programmable instructions to operate the computer or the data processing device.

In addition, each block or each operation may represent a module, a segment, or part of code that includes one or more executable instructions for executing specified logical functions. In some alternative embodiments, functions referred to with respect to blocks or operations may be performed in an order different from that described herein. For example, two blocks or operations illustrated consecutively may be performed substantially simultaneously or in a reverse order of functions corresponding thereto when necessary.

Hereinafter, embodiments of the present disclosure will be described in detail with reference to the accompanying drawings. However, the embodiments of the present disclosure described below may be modified in various other forms and the scope of the present disclosure is not limited thereto.

Embodiments of the present disclosure are provided to more fully describe the present disclosure to those of ordinary skill in the art.

FIG. 1 is a diagram illustrating a configuration of an image processing device according to an embodiment of the present disclosure.

An image processing device 1 is an electronic device capable of executing an image processing program. An image processing program according to an embodiment image-processes image data acquired through an intraoral scanner and guides a scan strategy for accurately photographing teeth by the intraoral scanner. The electronic device may be a computer, a notebook computer, a laptop computer, a tablet PC, a smartphone, a cellular phone, a personal media player (PMP), a personal digital assistant (PDA), or the like. The image processing program may include a scan program, a computer-aided design (CAD) program, or the like. The image processing device 1 is also applicable to programs for processing general medical images, as well an intraoral scanning. Furthermore, the image processing device 1 may be used to train scanning using the intraoral scanner.

The intraoral scanner scans the inside of a user's mouth to acquire image data of the inside of the mouth. The image processing device 1 receives image data from the intraoral scanner through a data acquisition unit 10 and processes the image data acquired by the intraoral scanner using a control unit 14. In addition, the image processing device 1 guides a scan strategy to accurately photograph teeth through the intraoral scanner. The intraoral scanner may drive a light source of an internal illumination to output light and emit the output light to the inside of a user's mouth or an intraoral model along an optical path. In this case, light reflected from the inside of the mouth or the intraoral model may reach an image sensor of the intraoral scanner along the optical path and thus image data of the inside of the mouth or the intraoral model may be acquired.

A configuration of an image processing device having the above-described characteristics will be described with reference to FIG. 1 below.

Referring to FIG. 1, the image processing device 1 according to an embodiment includes the data acquisition unit 10, a storage unit 12, the control unit 14, an input unit 16, and an output unit 18.

The data acquisition unit 10 acquires image data captured through the intraoral scanner. The intraoral scanner may be a three-dimensional (3D) scanner that scans a plaster model acquired by modeling a patient's mouth or may be a 3D intra-oral scanner that scans the inside of a patient's mouth. The acquired image data may be stored in the storage unit 12. The storage unit 12 stores information necessary to perform an operation of the image processing device 1 and information generated according to execution of the operation and provides information in response to a request from the control unit 14.

The control unit 14 receives image data acquired through the data acquisition unit 10 from the intraoral scanner, image-processes the image data, and guides a scanning strategy for accurately photographing teeth through the intraoral scanner. For example, guide scan paths providing scanning strategies of intraoral scanners are displayed on a guide screen. The guide scan paths may be set in advance in units of the manufacturers of the intraoral scanners. In this case, the guide scan paths are not provided in a separate document or on a web page but are displayed on a screen of an image processing program so that a user may check whether photographing is appropriately performed according to a guide while viewing the guide scan path on the screen.

The control unit 14 according to an embodiment tracks a user scan path and provides the user scan path to the output unit 18. The user scan path is a path actually scanned in real time when the user starts scanning through the intraoral scanner along the guide scan path. The control unit 14 tracks the user scan path and matches the tracked user scan path to the guide scan path so as to configure a scan guide screen. In this case, the output unit 18 may display the user scan path on the scan guide screen together with the guide scan path. For example, the guide scan path and the user scan path are displayed to be overlapped on teeth model data.

For example, in a method of tracking the user scan path, the control unit 14 generates a depth image by reconstructing a 2D image acquired through scanning by the intraoral scanner and connects central points or main points of objects constituting the depth image.

Next, intersection points from the central points or main points of the objects to a surface of a 3D object are detected and the detected intersection points are connected to generate a user scan path.

Furthermore, points spaced a predetermined distance from the detected intersection points may be connected to correct the user scan path. Embodiments of this method will be described with reference to FIG. 7 below. As another example, the control unit 14 may generate a user scan path by connecting central points of objects of a 3D image acquired through scanning by the intraoral scanner.

Image processing is performed to display a user scan path in a guide scan path. For example, the control unit 14 makes a scale of a tracked user scan path be the same as a scale of the guide scan path and matches the user scan path to the guide scan path. Embodiments of this method will be described with reference to FIGS. 9 and 10 below. The control unit 14 may compare and analyze the user scan path and the guide scan path to each other and provide at least one of a comparison and analysis result and a warning signal generated according to the result. For example, when the user scan path is quite different from the guide scan path, a warning signal is generated so that the user may notice this fact.

The output unit 18 may display the scan guide screen in various ways. For example, the output unit 18 may rotate the guide scan path according to a user's manipulation or may move the guide scan path to the same viewpoint as a position actually photographed by the intraoral scanner and display the guide scan path on the scan guide screen. In addition, the output unit 18 may rotate the guide scan path in real time and display the guide scan path on the scan guide screen in synchronization with a position actually photographed through the intraoral scanner. As another example, the output unit 18 may display, on a screen, a user interface through which a user may set whether to display a scan guide or not, and receive an instruction as to whether to display the scan guide or not from the user through the input unit 16. As another example, the output unit 18 may display on the screen a user interface through which a user may set a transparency of the scan guide and receive an instruction about a transparency of the scan guide from the user through the input unit 16. The output unit 18 may display a user scan path in real time on image data actually scanned through the intraoral scanner. The input unit 16 receives various user instructions through the image processing program.

Figure 2:
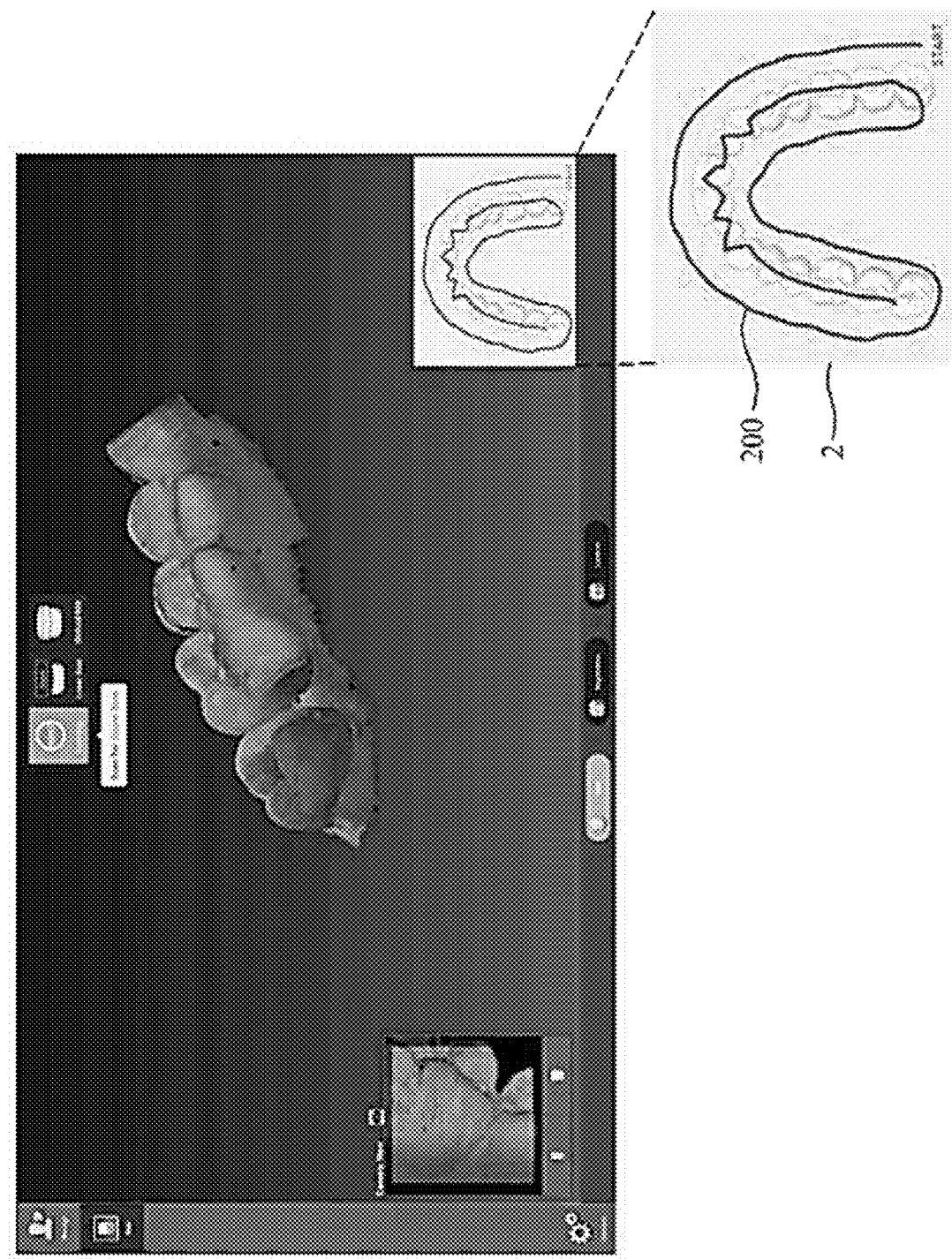
FIGS. 2 and 3 are diagrams illustrating a configuration of a scan guide screen and a setting screen according to an embodiment of the present disclosure.
Figure 3:
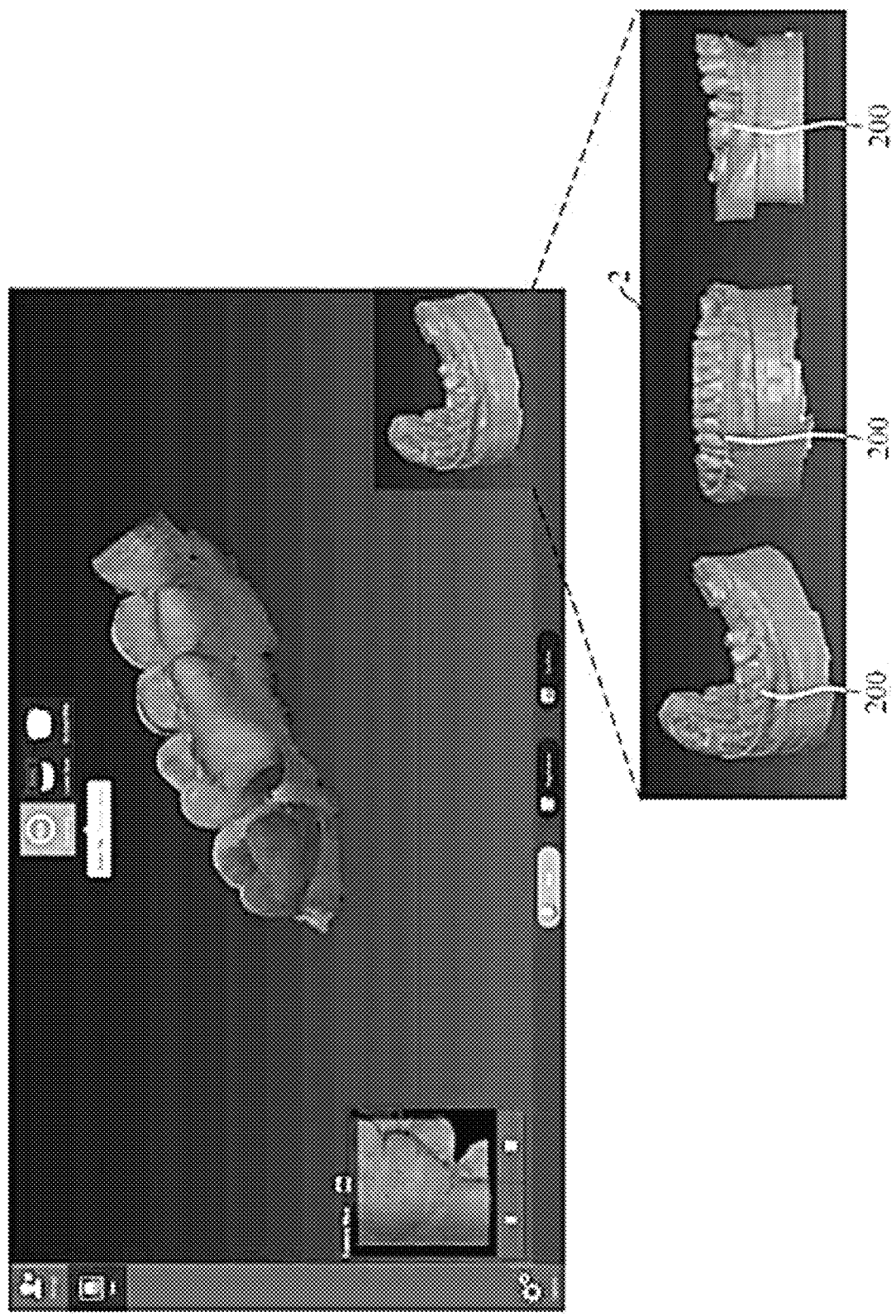

FIGS. 2 and 3 are diagrams illustrating a configuration of a scan guide screen and a setting screen according to an embodiment of the present disclosure. More particularly, FIG. 2 illustrates a two-dimensional (2D) scan guide screen. FIG. 3 illustrates a 3D scan guide screen.

Referring to FIGS. 2 and 3, a scan program displays, on a scan guide screen 2, a guide scan path 200 providing a scanning strategy so that a user may accurately photograph teeth through an intraoral scanner before and during scanning. In this case, the guide scan path 200 is displayed on teeth model data. The scanning strategy provided from the guide scan path 200 includes a scan start point, a scanning direction, a scan order, etc. The guide scan path 200 may be provided in the form of a two-dimensional (2D) or three-dimensional (3D) image or provided in an animation form. A user may perform scanning along the guide scan path 200.

The scan guide screen 2 may be provided as a default at one of four corners of the scan program. The user may move the scan guide screen 2 to a desired position. For example, the scan guide screen 2 may be moved freely using a drag-and-hold function.

As shown in FIG. 2, a 2D scan guide screen 2 is based on a top view and may be switched to another view. As shown in FIG. 3, a guide scan path 200 of a 3D scan guide screen 2 may be rotated in view according to a user input or may be moved to and displayed at the same viewpoint as a position actually photographed through an intraoral scanner. Furthermore, the 3D scan guide screen 2 may be synchronized with a position actually photographed through the intraoral scanner to rotate and display the guide scan path 200 in real time.

Figure 4:
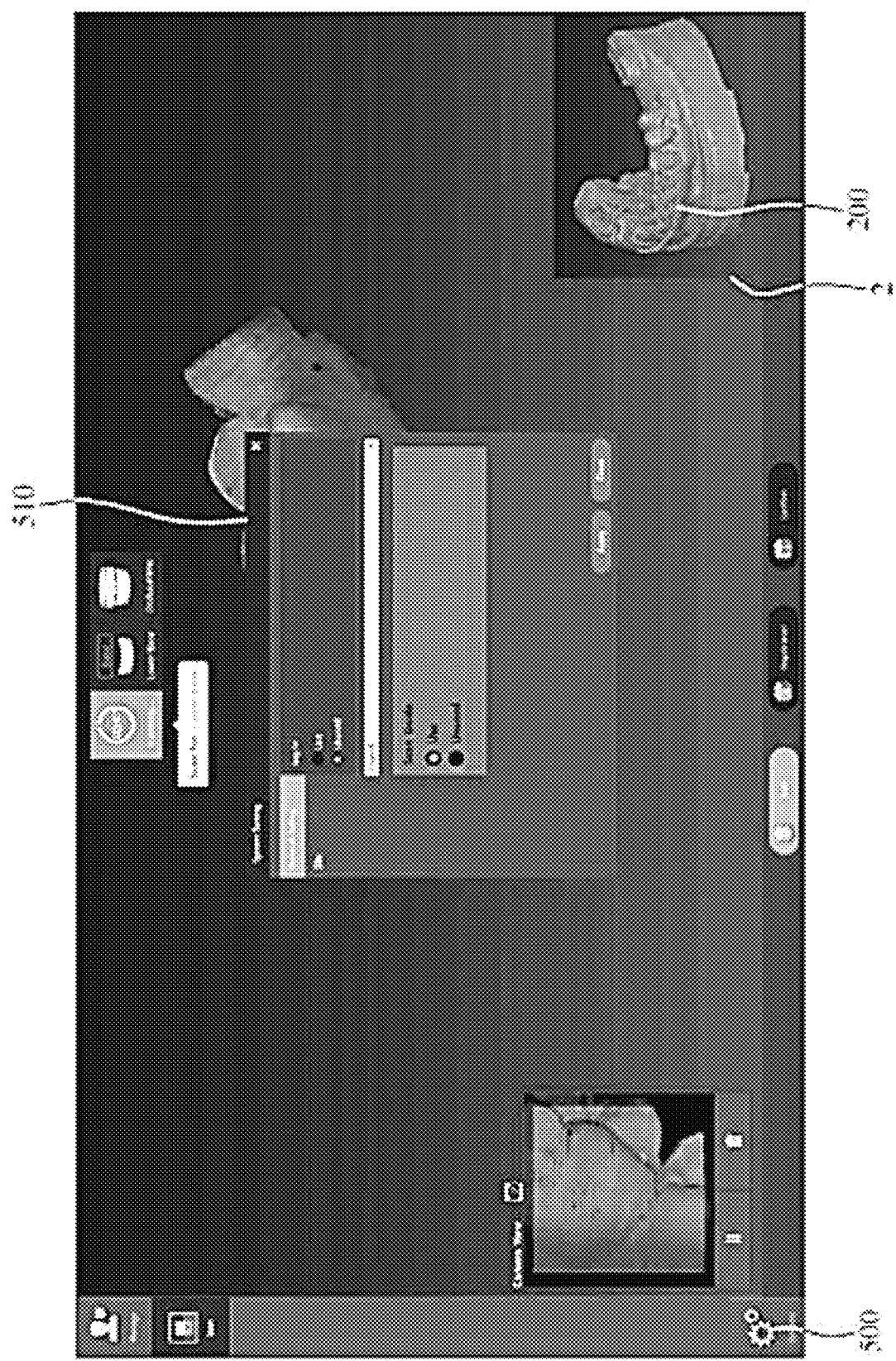
FIGS. 4 and 5 are diagrams illustrating scan guide on/off functions according to various embodiments of the present disclosure.
Figure 5:
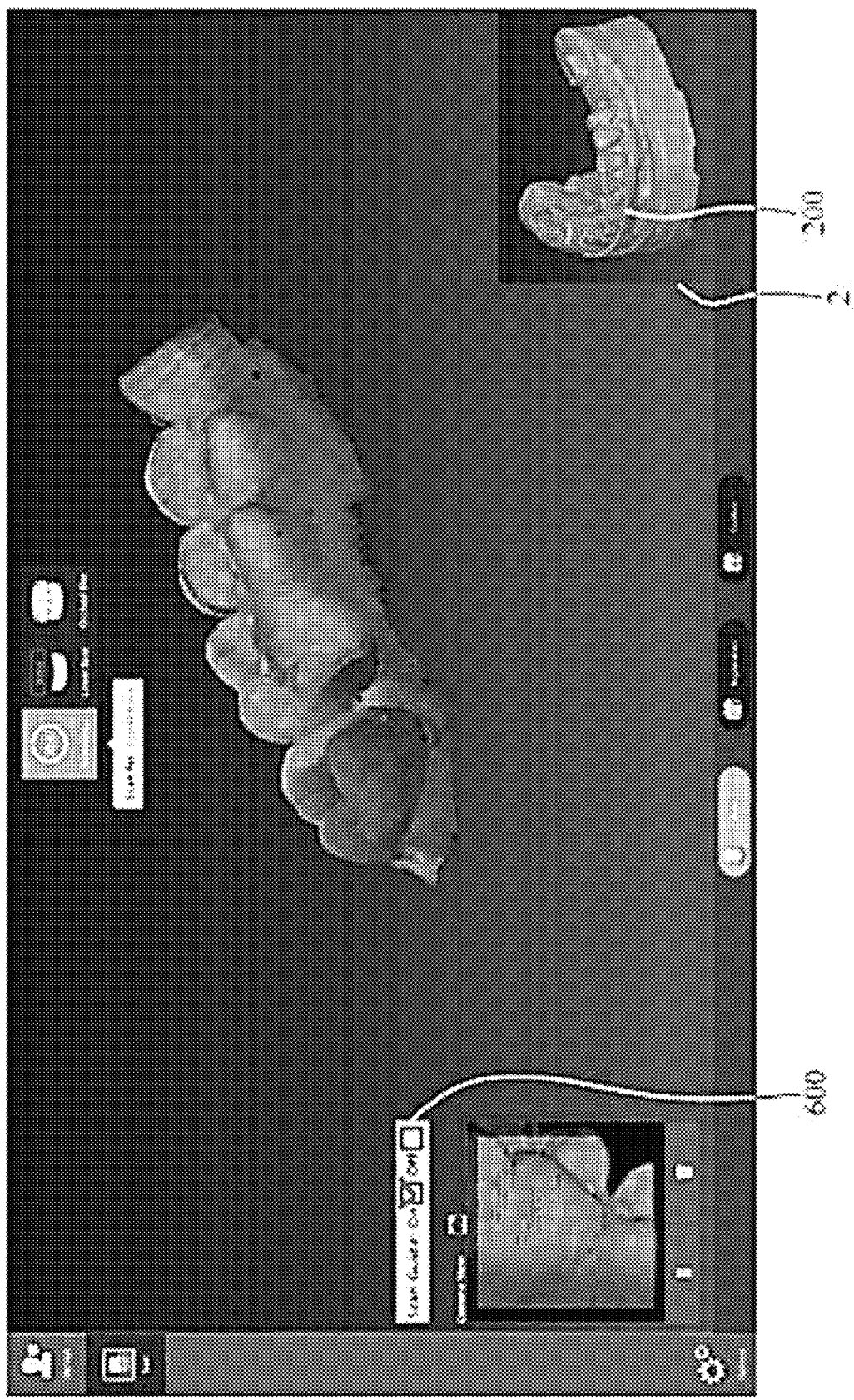

FIGS. 4 and 5 are diagrams illustrating scan guide on/off functions according to various embodiments of the present disclosure.

Referring to FIGS. 4 and 5, a user may want a scan guide screen 2 to not be visible on a scan program. In this case, as shown in FIG. 4, a scan guide screen may be turned on or off through a setting window 510 of a separate option menu 500. As another example, as shown in FIG. 5, a user interface for processing an on/off function in real time, e.g., a setting window 600 with a checkbox-type button, may be provided on a scan screen so that a user may turn on/off a scan guide screen. Furthermore, a user interface through which a user may set a transparency of a guide scan path 200 of the scan guide screen 2 may be displayed on a screen to receive an instruction about a transparency of a scan guide from the user. This is a case in which the user wants the guide scan path 200 to be visible but also wants a teeth model to be clearly visible, and thus may be achieved through transparency control.

Figure 6:
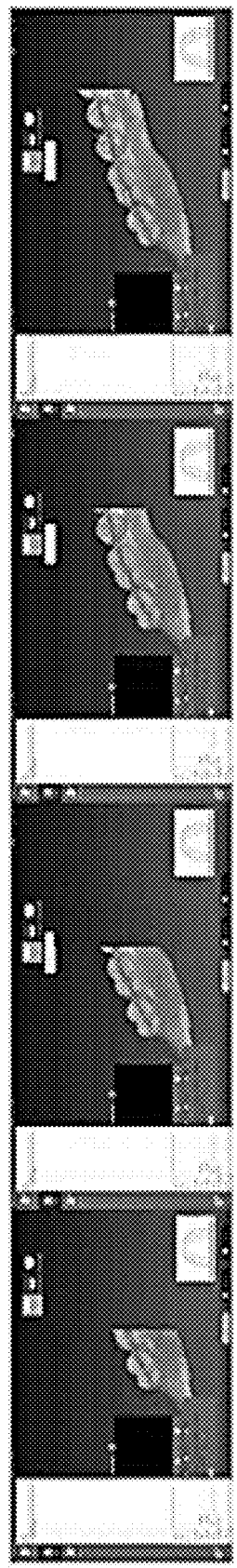
FIG. 6 is a diagram illustrating a screen for tracking a user scan path according to an embodiment of the present disclosure.

FIG. 6 is a diagram illustrating a screen for tracking a user scan path according to an embodiment of the present disclosure.

Referring to FIG. 6, as scanning is being performed, a scan path photographed by a user may be tracked in real time and displayed on a scan guide screen 2 and may be displayed on actually scanned image data.

Figure 7:
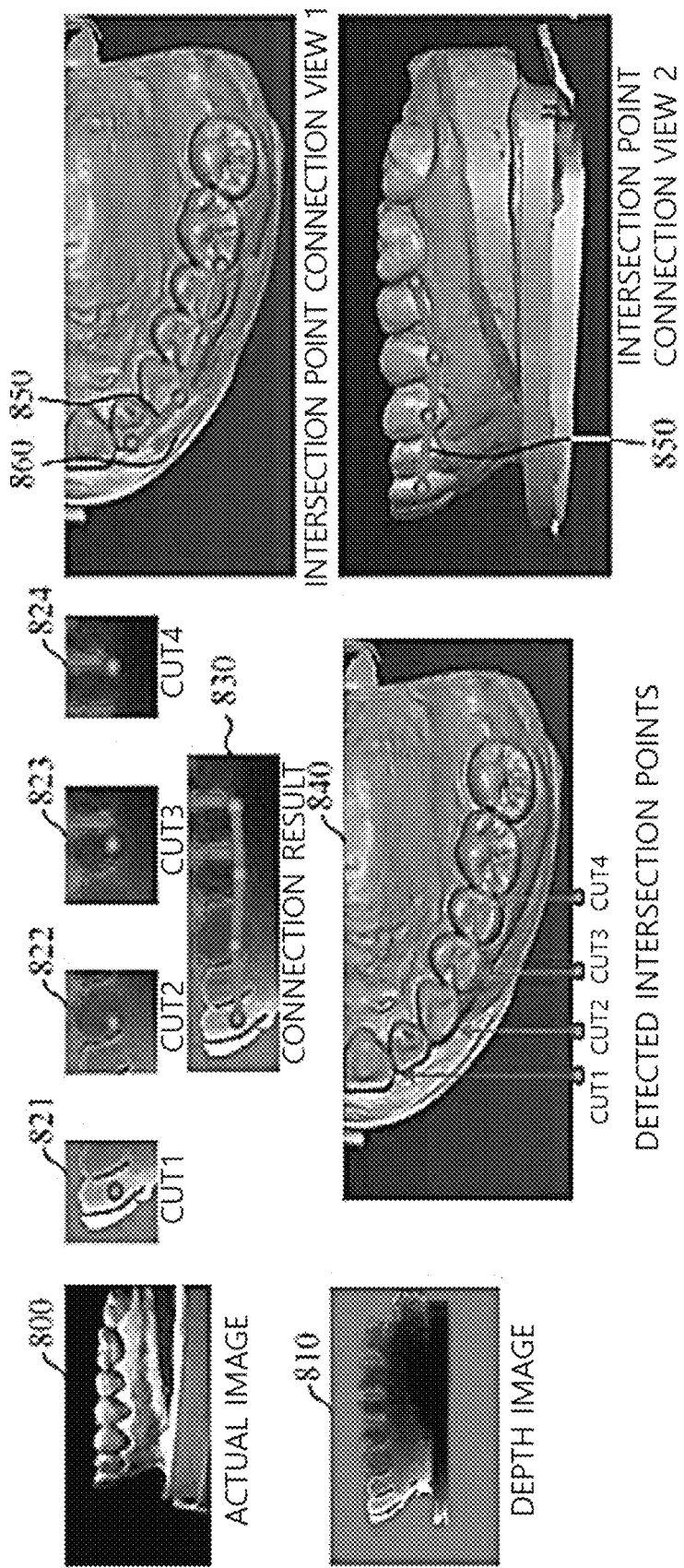
FIG. 7 is a diagram illustrating a program screen for describing an algorithm for tracking a user scan path according to an embodiment of the present disclosure.

FIG. 7 is a diagram illustrating a program screen for describing an algorithm for tracking a user scan path according to an embodiment of the present disclosure.

Referring to FIGS. 1 and 7, the image processing device 1 may track a user scan path using a method of tracking a path by selecting a center of an image, and display the user scan path on a screen. For example, as shown in FIG. 7, central points on a depth image 810 are connected. The depth image 810 is an image having a height (Z value) and may be acquired based on various reconstruction algorithms for 2D images. A 3D object may be acquired using the depth image 810. When a resolution of an intraoral scanner camera is 640*480, depth image cuts having overlapping regions have a size of 640*480. 320*240 points 821, 822, 823, and 824, which are central points (or main points) on the depth image cuts acquired after reconstruction are sequentially connected (830). Thereafter, for 3D representation, intersection points from the central points 821, 822, 823, and 824 on the depth image cuts to a point on a surface of a 3D object are detected (840) and detected intersection points are sequentially connected to generate a user scan path 850. In this case, when the intersection points are connected according to the positions thereof, a line connecting the intersection points (e.g., 850 of intersection point connection views 1 and 2) may pass through the 3D object. Thus, the user scan path may be corrected by adding a predetermined distance, e.g., a 5 mm distance, thereto (e.g., 860 of the intersection point connection view 1). In the example of FIG. 7, points are displayed together but may not be output and only lines may be output when a program is actually executed.

Figure 8:
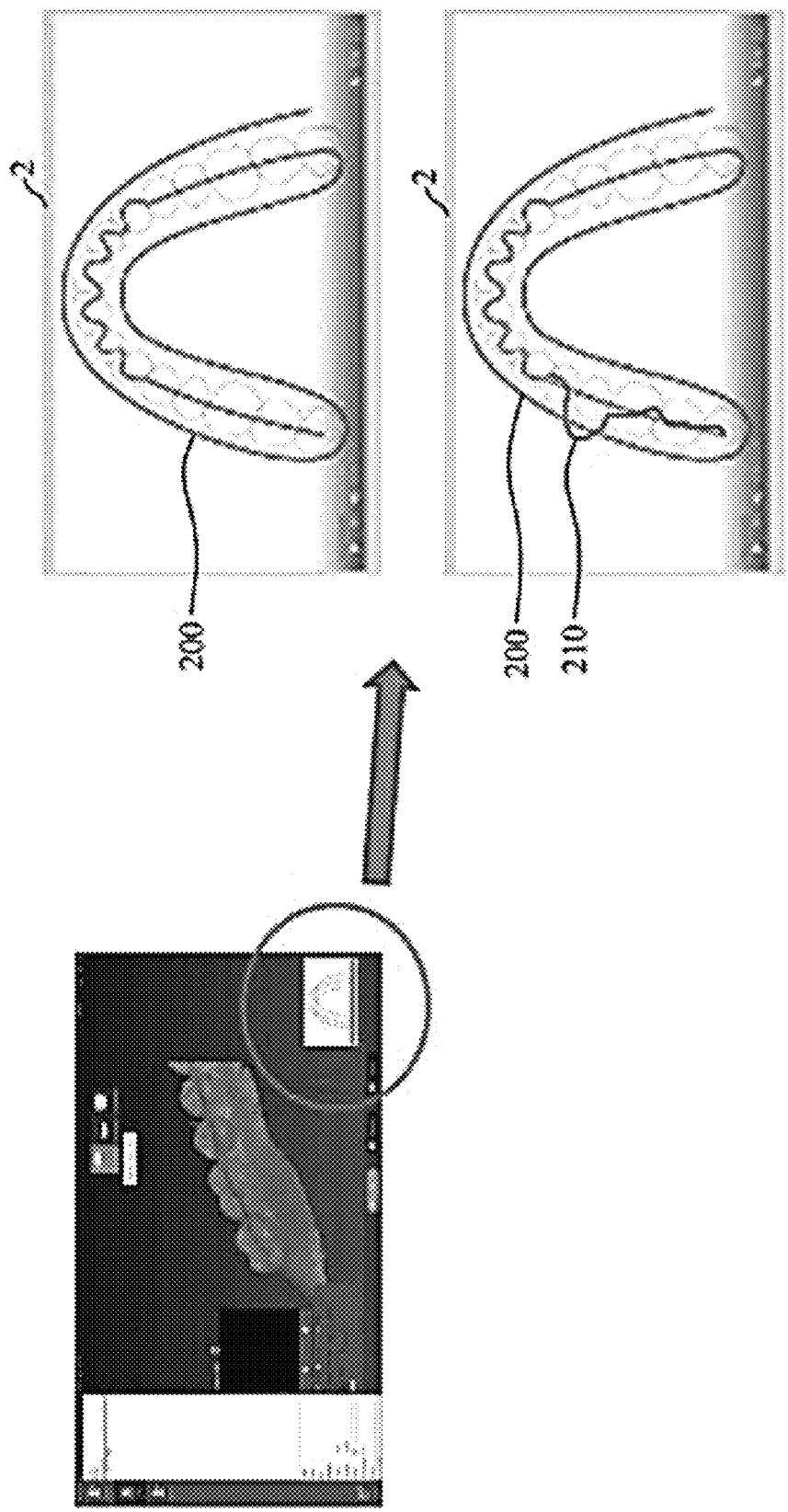
FIG. 8 is a diagram illustrating a scan screen for comparing a tracked user scan path and a guide scan path and outputting a comparison result according to an embodiment of the present disclosure.

FIG. 8 is a diagram illustrating a scan screen for comparing a tracked user scan path and a guide scan path and outputting a comparison result according to an embodiment of the present disclosure.

Referring to FIGS. 1 and 8, the image processing device 1 displays a user scan path 210 and a guide scan path 200 together on teeth model data displayed on a scan guide screen 2. In this case, as the user scan path 210 and the guide scan path 200 are superimposed, a user may compare the user scan path 210 and the guide scan path 200 to each other to check on the fly whether scanning is being accurately performed by the user.

The image processing device 1 according to an embodiment may compare and analyze the user scan path 210 and the guide scan path 200 to each other and provide a comparison and analysis result to the user. For example, a distance between a point on the user scan path 210 and a point on the guide scan path 200 that match each other with respect to a certain point on the teeth model data is calculated and displayed. Furthermore, the image processing device 1 may output a warning signal about the comparison and analysis result. For example, when the calculated distance is greater than a predetermined distance, it is determined that scanning was performed abnormally and the user is warned of this fact. For the warning signal, a general notification technique such as alarm, displaying a pop-up menu, or the like may be used.

Figure 9:
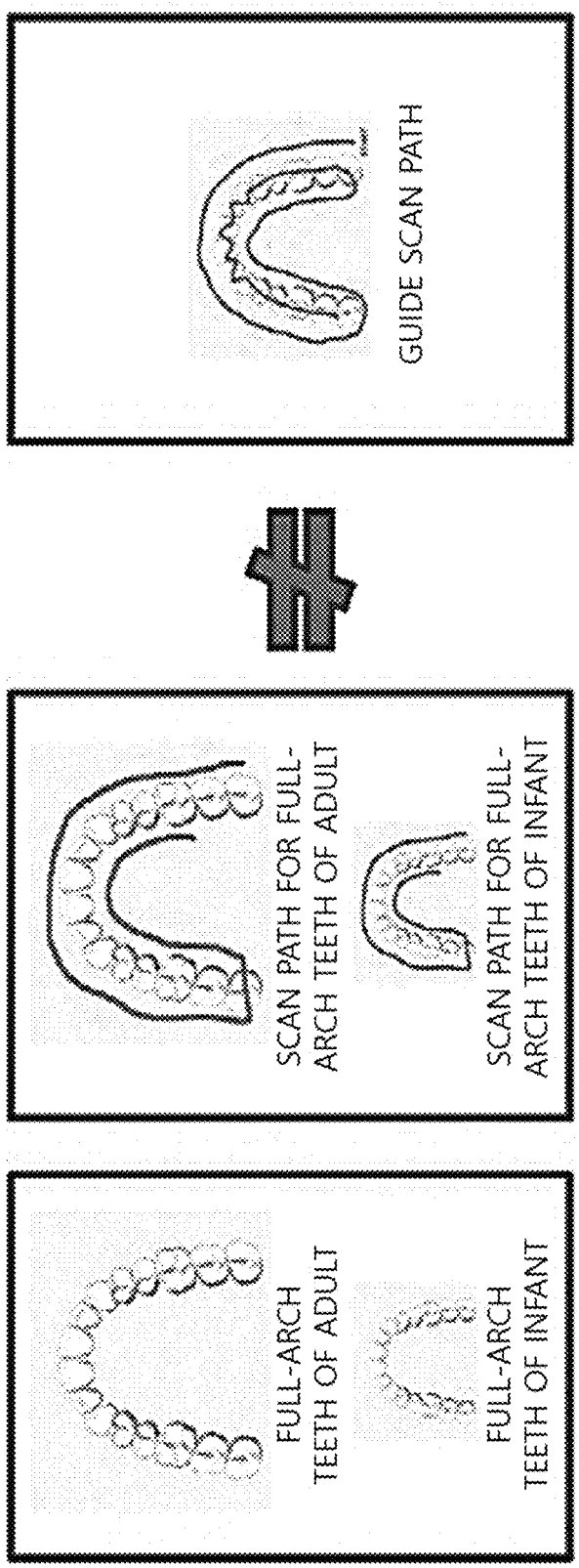
FIG. 9 is a diagram illustrating a mismatch between a user scan path and a guide scan path of a user.

FIG. 9 is a diagram illustrating a mismatch between a user scan path and a guide scan path of a user.

Referring to FIG. 9, a scale of a scan path may vary because a full arch size, a tooth size, a teeth array, etc. of each person are different. For example, as shown in FIG. 9, a scale of a user scan path used for a full-arch teeth of an adult is different from a scale of a user scan path used for full-arch teeth of an infant (which is smaller than that of the adult) and thus does not match a guide scan path. Therefore, scale equalization is required.

Figure 10:
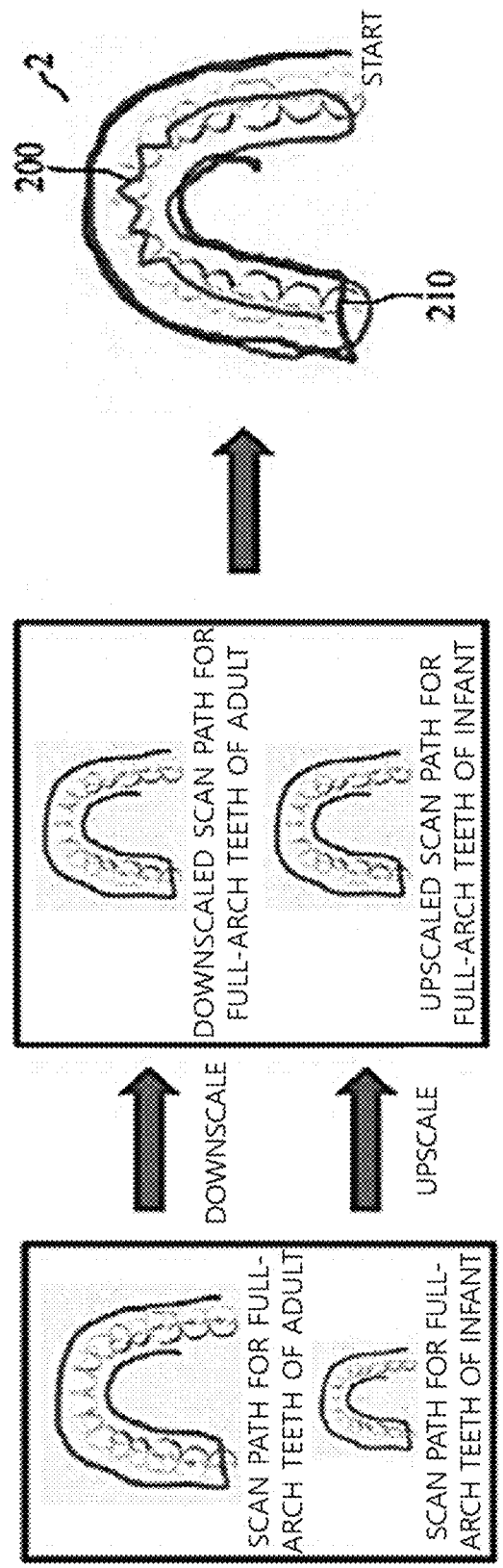
FIG. 10 is a diagram illustrating a screen for matching a user scan path and a guide scan path according to an embodiment of the present disclosure.

FIG. 10 is a diagram illustrating a screen for matching a user scan path and a guide scan path according to an embodiment of the present disclosure.

Referring to FIGS. 1 and 10, it is assumed that a user starts scanning at the same position as a starting point suggested by a guide scan path to fix a scale mismatch described above with reference to FIG. 9. For scale equalization, the image processing device 1 according to an embodiment adjusts a scale such that a ratio between horizontal and vertical lengths of a user scan path may be the same as a ratio between horizontal and vertical lengths of the guide scan path. For example, a downscaled user scan path is created by downscaling a user scan path formed for full-arch teeth of an adult. An upscaled user scan path is created by upscaling a user scan path formed for full-arch teeth of an infant. A scale of a user scan path 210 created by up/downscaling a user scan path matches that of a guide scan path 200 and thus the user scan path 210 may match the guide scan path 200 in a scan guide screen 2.

Figure 11A:
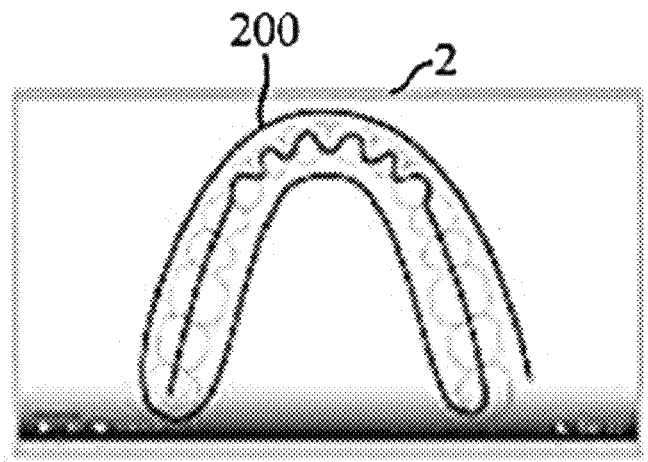
FIGS. 11A-11C are diagrams illustrating a screen showing a comparison between a user scan path and a guide scan path according to an embodiment of the present disclosure.
Figure 11B:
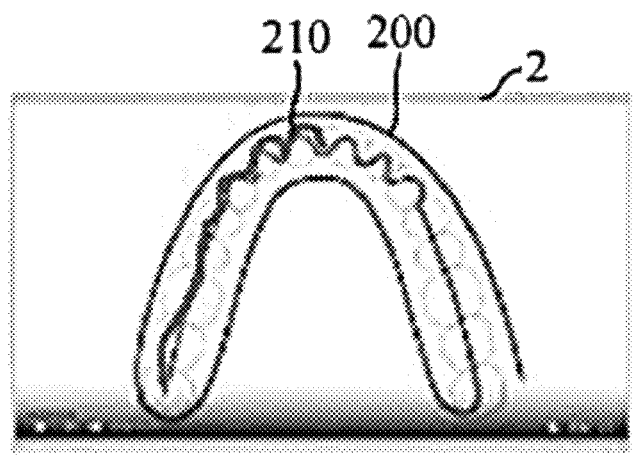
Figure 11C:
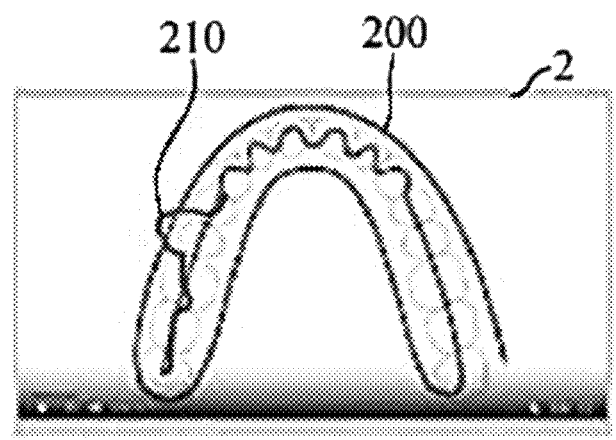

FIGS. 11A-11C are diagrams illustrating a screen showing a comparison between a user scan path and a guide scan path according to an embodiment of the present disclosure.

Referring to FIGS. 1 and 11A-11C, the image processing device 1 displays a guide scan path 200 for scanning on a guide scan screen 2 (FIG. 11A) and displays a user scan path 210, which is created when a user starts scanning along the guide scan path 200, together with the guide scan path 200 on the guide scan screen 2 (FIGS. 11B and 11C). FIG. 11B illustrates a case in which photographing is appropriately performed by a user along the guide scan path 200, and FIG. 11C illustrates a case in which photographing is performed by the user out of the guide scan path 200.

Figure 12:
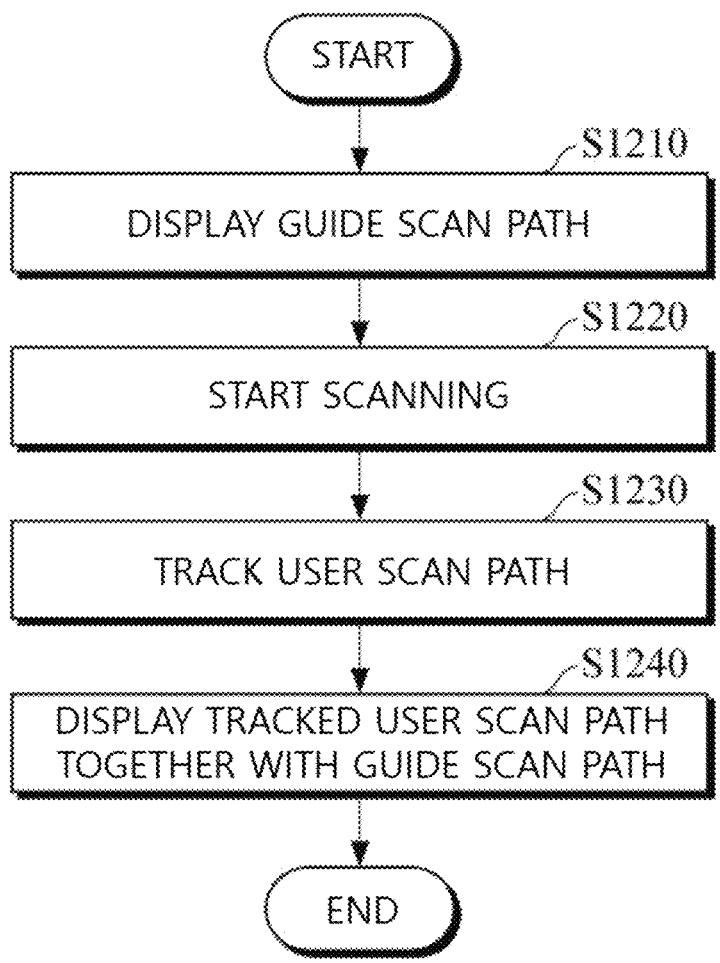
FIG. 12 is a flowchart of a scan guide providing method according to an embodiment of the present disclosure.

FIG. 12 is a flowchart of a scan guide providing method according to an embodiment of the present disclosure.

Referring to FIGS. 1 and 12, the image processing device 1 displays, on a scan screen, a guide scan path providing a scanning strategy of an intraoral scanner (S1210). In the displaying of the guide scan path on the screen (S1210), the image processing device 1 may display, on a screen, guide scan paths set in advance in units of the manufacturers of intraoral scanners. For example, the image processing device 1 may rotate the guide scan path according to a user's manipulation or may move the guide scan path to the same viewpoint as a position actually photographed by the intraoral scanner and display the guide scan path on the screen. As another example, the image processing device 1 may rotate the guide scan path in real time and display the guide scan path on the screen in synchronization with a position actually photographed through the intraoral scanner. Furthermore, the image processing device 1 may display, on the screen, a user interface through which a user may set whether to display a scan guide or not, a user interface through which a user may set a transparency of the scan guide, etc.

Thereafter, when scanning is started (S1220), the image processing device 1 tracks a user scan path actually scanned through the intraoral scanner along the guide scan path (S1230).

In the tracking of the user scan path (S1230), the image processing device 1 according to an embodiment tracks the user scan path using a central point or a main point on an image. For example, the image processing device 1 creates a depth image by reconstructing a 2D image acquired through scanning by the intraoral scanner and connects central points or main points on objects constituting the depth image. Next, intersection points from the central points or main points on the objects to a point on a surface of a 3D object are detected and detected intersection points are connected to generate a user scan path. In this case, points spaced a predetermined distance from the detected intersection points may be connected to correct the user scan path. As another example, the image processing device 1 may generate a user scan path by connecting central points on objects of a 3D image acquired through scanning by the intraoral scanner.

Next, the image processing device 1 displays the tracked user scan path together with the guide scan path (S1240). In the displaying of the tracked user scan path together with the guide scan path (S1240), the image processing device 1 according to an embodiment equalizes a scale of the user scan path with that of the guide scan path and displays the user scan path to match the guide scan path. The image processing device 1 may display the user scan path on image data actually scanned through the intraoral scanner.

Furthermore, the image processing device 1 may compare and analyze the user scan path and the guide scan path to each other and provide at least one of a comparison and analysis result and a warning signal.

The present disclosure has been described above with respect to embodiments thereof. It will be understood by those of ordinary skill in the art that the present disclosure may be embodied in many different forms without departing from essential features of the present disclosure. Therefore, the embodiments set forth herein should be considered in a descriptive sense only and not for purposes of limitation. The scope of the present disclosure is set forth in the claims rather than in the foregoing description, and all differences falling within a scope equivalent thereto should be construed as being included in the present disclosure.

The invention claimed is:

1. A scan guide providing method comprising:
    displaying, on a scan screen, a guide scan path providing a scanning strategy of an intraoral scanner;
    tracking a user scan path scanned through the intraoral scanner along the guide scan path; and
    displaying the tracked user scan path together with the guide scan path,
    wherein the tracking of the user scan path comprises:
    creating a depth image by reconstructing a two-dimensional (2D) image acquired through scanning by the intraoral scanner;
    connecting central points or main points of objects constituting the depth image; and
    generating the user scan path by detecting intersection points from the central points or main points on the objects to a position on a surface of a three-dimensional (3D) object and connecting the detected intersection points.

2. The scan guide providing method of claim 1, wherein the displaying of the guide scan path on the scan screen comprises displaying, on a screen, guide scan paths set in advance for respective manufacturers of intraoral scanners.

3. The scan guide providing method of claim 1, wherein the displaying of the guide scan path on the scan screen comprises rotating the guide scan path according to a user's manipulation or moving the guide scan path to the same viewpoint as a position actually photographed by the intraoral scanner and displaying the guide scan path on a screen.

4. The scan guide providing method of claim 1, wherein the displaying of the guide scan path on the scan screen comprises rotating the guide scan path in real time and displaying the guide scan path on a screen in synchronization with a position actually photographed by the intraoral scanner.

5. The scan guide providing method of claim 1, wherein the tracking of the user scan path further comprises correcting the user scan path by connecting points spaced a predetermined distance from the detected intersection points.

6. The scan guide providing method of claim 1, wherein the tracking of the user scan path comprises generating the user scan path by connecting the central points on objects constituting a three-dimensional (3D) image acquired through scanning by the intraoral scanner.

7. The scan guide providing method of claim 1, wherein the displaying of the tracked user scan path together with the guide scan path comprises equalizing a scale of the tracked user scan path with a scale of the guide scan path and displaying the user scan path to match the guide scan path.

8. The scan guide providing method of claim 1, further comprising displaying the user scan path on image data acquired through scanning by the intraoral scanner.

9. The scan guide providing method of claim 1, further comprising:
    providing a user interface through which whether to display a scan guide or not is set by a user; and
    providing a user interface through which a transparency of the scan guide is set by the user.

10. The scan guide providing method of claim 1, further comprising:
  comparing and analyzing the user scan path and the guide scan path to each other; and
  providing at least one of a comparison and analysis result and a warning signal generated as the result.

11. An image processing device comprising:
  a data acquisition unit configured to acquire, from an intraoral scanner, image data acquired by scanning an inside of a user's mouth or an intraoral model;
  an output unit configured to display the image data acquired from the intraoral scanner and a guide scan path providing a scanning strategy of the intraoral scanner; and
  a control unit configured to receive and image-process the image data acquired by the data acquisition unit and providing the guide scan path to the output unit,
  wherein the control unit configures a screen by tracking a user scan path scanned through the intraoral scanner along the guide scan path and matching the tracked user scan path to the guide scan path, and
  the output unit displays the user scan path on the screen together with the guide scan path, and
  wherein the control unit creates a depth image by reconstructing a two-dimensional (2D) image acquired through scanning by the intraoral scanner, connects central points or main points on objects constituting the depth image, and generates the user scan path by detecting intersection points from the central points or main points on the objects to a position on a surface of a three-dimensional (3D) object and connecting the detected intersection points.

12. The image processing device of claim 11, wherein the output unit rotates the guide scan path according to a user's manipulation or moves the guide scan path to the same viewpoint as a position actually photographed through the intraoral scanner and displays the guide scan path on the screen.

13. The image processing device of claim 11, wherein the output unit rotates the guide scan path in real time and displays the guide scan path on the screen in synchronization with a position actually photographed by the intraoral scanner.

14. The image processing device of claim 11, wherein the output unit displays, on the screen, a user interface through which whether to display a scan guide or not is set by a user and a user interface through which a transparency of the scan guide is set by the user.

15. The image processing device of claim 11, wherein the control unit corrects the user scan path by connecting points spaced a predetermined distance from the detected intersection points.

16. The image processing device of claim 11, wherein the control unit generates the user scan path by connecting the central points on objects constituting a three-dimensional (3D) image acquired through scanning by the intraoral scanner.

17. The image processing device of claim 11, wherein the control unit equalizes a scale of the tracked user scan path with a scale of the guide scan path and matches the user scan path to the guide scan path.

18. The image processing device of claim 11, wherein the output unit displays the user scan path on image data acquired through scanning by the intraoral scanner.

19. The image processing device of claim 11, wherein the control unit compares and analyzes the user scan path and the guide scan path to each other and provides at least one of a comparison and analysis result and a warning signal generated as a result.

* * * * *